United States Patent [19]
Smith

[11] 4,445,359
[45] May 1, 1984

[54] SYSTEM AND PROCESS FOR CALIBRATING A COMBUSTION GAS ANALYZER
[75] Inventor: Vigo N. Smith, Saratoga, Calif.
[73] Assignee: Measurex Corporation, Cupertino, Calif.
[21] Appl. No.: 291,154
[22] Filed: Aug. 7, 1981
[51] Int. Cl.³ .............................................. G01N 21/17
[52] U.S. Cl. ..................................... 73/1 G; 356/437; 431/12
[58] Field of Search ................. 73/1 G, 1 R; 364/571; 250/373; 356/433, 434, 437, 438; 431/12, 76, 75, 79

[56] References Cited
U.S. PATENT DOCUMENTS

| | | | |
|---|---|---|---|
| 3,242,715 | 3/1966 | Hubner | 73/1 G |
| 3,359,784 | 12/1967 | Jorre et al. | 73/1 G |
| 3,807,876 | 4/1974 | Nakahara et al. | 356/437 |
| 3,899,252 | 8/1975 | Dimeff | 250/373 X |
| 4,359,950 | 11/1982 | Leffler et al. | 110/188 |

OTHER PUBLICATIONS

Process ICO Conference, *Optical Methods in Science and Industry Measurement*, Tokyo, 1974, J. Applied Physics, 14(1975).
Supplement 14-1, "A Novel Gas Analyzer for $SO_2$, NO and $NO_2$ in the Stack Effluent", pp. 131–136.

Primary Examiner—Gerald Goldberg
Assistant Examiner—Brian R. Tumm
Attorney, Agent, or Firm—Hal J. Bohner

[57] ABSTRACT

A system and process for calibrating a computer-based combustion gas analyzer is disclosed. The process includes introducing a series of gas samples into the analyzer, each sample containing a known concentration of a particular gas. The output of the analyzer is recorded and compared with the known gas concentrations to compute calibration coefficients which are used to calibrate the analyzer.

7 Claims, 2 Drawing Figures

SYSTEM AND PROCESS FOR CALIBRATING A COMBUSTION GAS ANALYZER

BACKGROUND OF THE INVENTION

1. Field of the Invention

This invention concerns a system for determining the concentration of a particular gas in a flowing stream of gases.

2. Description of the Prior Art

Energy is often produced by the combustion of fossil fuels, and the combustion process generates gases which are discharged through a stack to the atmosphere. The exhaust gases are normally a mixture of chemical compounds including, for example, carbon monoxide, carbon dioxide, sulphur dioxide, nitrogen oxide and other gases as well as solid particles. Regulatory agencies often require that no more than specified maximum quantities of the gases and particulates be discharged through the stack to the atmosphere. Consequently, to comply with such regulations, it is necessary to determine the concentration of particular combustion gases in the stream of gases in the stack.

There are known analyzers to measure the concentration of combustion gases in a stack. Before such analyzers can be used to achieve accurate results they must be calibrated. The calibration process can include introducing a series of gas samples into the analyzer while the analyzer is in operation and recording the output of the analyzer in response to each member of the series of samples. Utilizing the concentrations of a particular gas in the series of analyzed gases a graph is constructed depicting the relationship between the actual concentrations of the gas of interest and the output of the analyzer. Thus a person operating the analyzer can use the graph to determine the concentration of a particular gas in a sample which is analyzed based upon the output of the analyzer.

One major shortcoming of the calibration process described above is that it relies upon an operator's judgement to fit a curve to data points. This is frequently subject to error. Another shortcoming is that the graph can only be utilized by a person, and is not readily readable by a machine. Thus, values of the concentration determined from the graph are susceptible to error.

OBJECTS OF THE INVENTION

An object of the present invention is to provide a system and process for calibrating a combustion gas analyzer accurately and efficiently.

Another object of the present invention is to provide a system and process to automatically calibrate a combustion gas analyzer using information generated by a computer.

Further objects and advantages of the present invention may be ascertained by reference to the specification and drawings which are offered by way of example and not in limitation of the invention which is defined by the claims and equivalents thereto.

DETAILED DESCRIPTION OF THE PREFERRED EMBODIMENT

Figure 1:
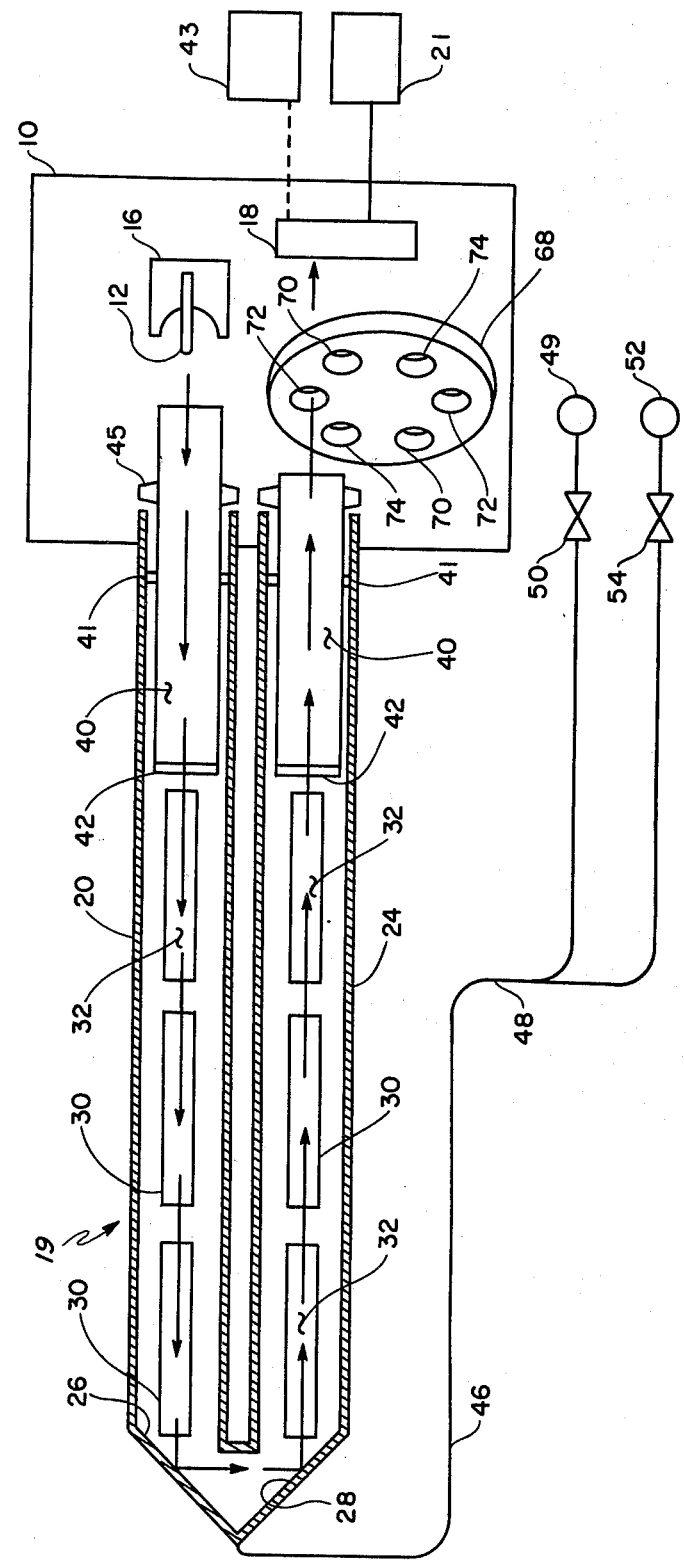
FIG. 1 is a schematic side view of a gas analyzer and calibration system of the present invention shown cut away.

With reference to FIG. 1, there is shown a combustion gas analyzer which is appropriate for calibration according to the process which will be discussed hereinafter. The illustrated combustion gas analyzer, taught in U.S. patent application Ser. No. 266,776 filed May 26, 1981, which is incorporated by reference herein, includes a support frame 10 having mounted thereon a light source 12 coupled to a reflector 16 for collimating the light and directing it. As used herein, the word "light" includes infrared, visible, ultraviolet and other similar electromagnetic radiation. Also coupled to the support frame near the source 12 is a detector 18 for detecting light from the source 12 and generating an electrical signal corresponding to the intensity thereof. Coupled to the detector 18 is a computer operating system 21 for receiving and processing the signal from the detector. Also coupled to the support frame 10 is a probe 19 which includes an upper light pipe 20 and a lower light pipe 24. The light pipes 20 and 24 include cylinders having their interior surfaces formed of buffed metal. The upper light pipe 20 is located with its right end adjacent to the light source 12 so that the light collimated by the reflector 16 is received by the right end of the light pipe 20 to travel through the light pipe from right to left according the arrows in FIG. 1.

At the left end of the upper light pipe 20 there is coupled an upper reflection means 26. The reflection means or mirror 26 includes a flat metal plate having its interior surface formed of buffed metal. Coupled to the lower side of the upper reflection means 26 is a lower reflection means or mirror 28 which, like the upper reflector means 26, is formed of buffed metal.

The lower light pipe 24 is coupled at its left end to the right side of lower mirror 28. Thus, the upper and lower reflector means 26 and 28 form a gas-tight connection between the left ends of the upper and lower light pipes 20 and 24. Also, the upper and lower reflector means 26 and 28 provide reflecting surfaces to reflect light from the left end of upper light pipe 20 downward into the lower light pipe 24 and therethrough. The right end of the lower light pipe 24 is coupled to the support frame adjacent to the detector 18 so that substantially all light leaving the right end of the light pipe 24 impinges upon the detector 18.

Three ports 30 are formed in each side of each light pipes 20 and 24. Pieces of gas-permeable material 32 are affixed on the outside of the light pipes to permit the passage of gas but not particulate material through the ports 30. In practice, a preferable material for forming the permeable material 32 is porous stainless steel felt which have been found to permit the passage of gas while permitting no substantial particulate material to pass therethrough.

Seal means including a cylinder 40 and a disk 42 are disposed in the right ends of each of the light pipes 20 and 24. In particular, each cylinder 40 has an open right end and is sealed closed on its left end by a disk 42. The cylinders 40 have raised portions 45 near their right ends so that cylinders 40 can be inserted into the light pipes a predetermined distance until the raised portions contact the light pipes. Each cylinder 40 is sized to fit snugly inside a light pipe, and o-rings 41 cooperate with the cylinders and light pipes to aid sealing. Thus gas is prevented from leving the right ends of the light pipes.

The analyzer includes a rotable disc 86 which contains three hollow, cylindrical containers 70, 72 and 74. The disc 68 is mounted adjacent the detector 18 so that as the disc rotates the container 70, 72 and 74 are sequentially interposed in the beam of radiation before it reaches the detector 18. In the present embodiment cylinder 70 is filled with substantially pure nitrogen ($N_2$), cylinder 72 is filled with substantially pure carbon monoxide (CO) and cylinder 74 is filled with substantially pure carbon dioxide ($CO_2$).

With further reference to FIG. 1, the calibration system is schematically illustrated coupled to the probe 19. The calibration system includes a calibration computer system 43 which can be selectively coupled to receive signals from the detector 18. (The calibration computer system 43 is different from the computer operating system 21. However, the same computer could be programmed to perform the functions of both computers 21 and 43.) The calibration system further includes conduit 46 connected in gas flow communication to the probe 19 at the junction of the mirrors 26 and 28. The conduit 46 is coupled to a tee 48 which in turn is coupled to valves 50 and 54. Valve 50 is coupled to a source of gas 49, and valve 54 is coupled to a different source of gas 52.

When the analyzer is used to analyze combustion gases, the probe 19 is inserted into a stack or the like which contains a stream of flowing gases. Gases permeate through the gas permeable material 32, thereby filling the light pipes 20 and 24 with gas which is the same as the gas in the stack 60 except that the gas within the light pipes 20 and 24 contains no substantial concentration of particulates.

The light source 12 generates a beam of light which travels through the light pipes as shown by the arrows and impinges upon the detector 18. In practice, if it is desired to measure the concentrations of carbon monoxide (CO) and carbon dioxide ($CO_2$) for example, the light emited by the source 12 should be in the infrared range.

Figure 2:
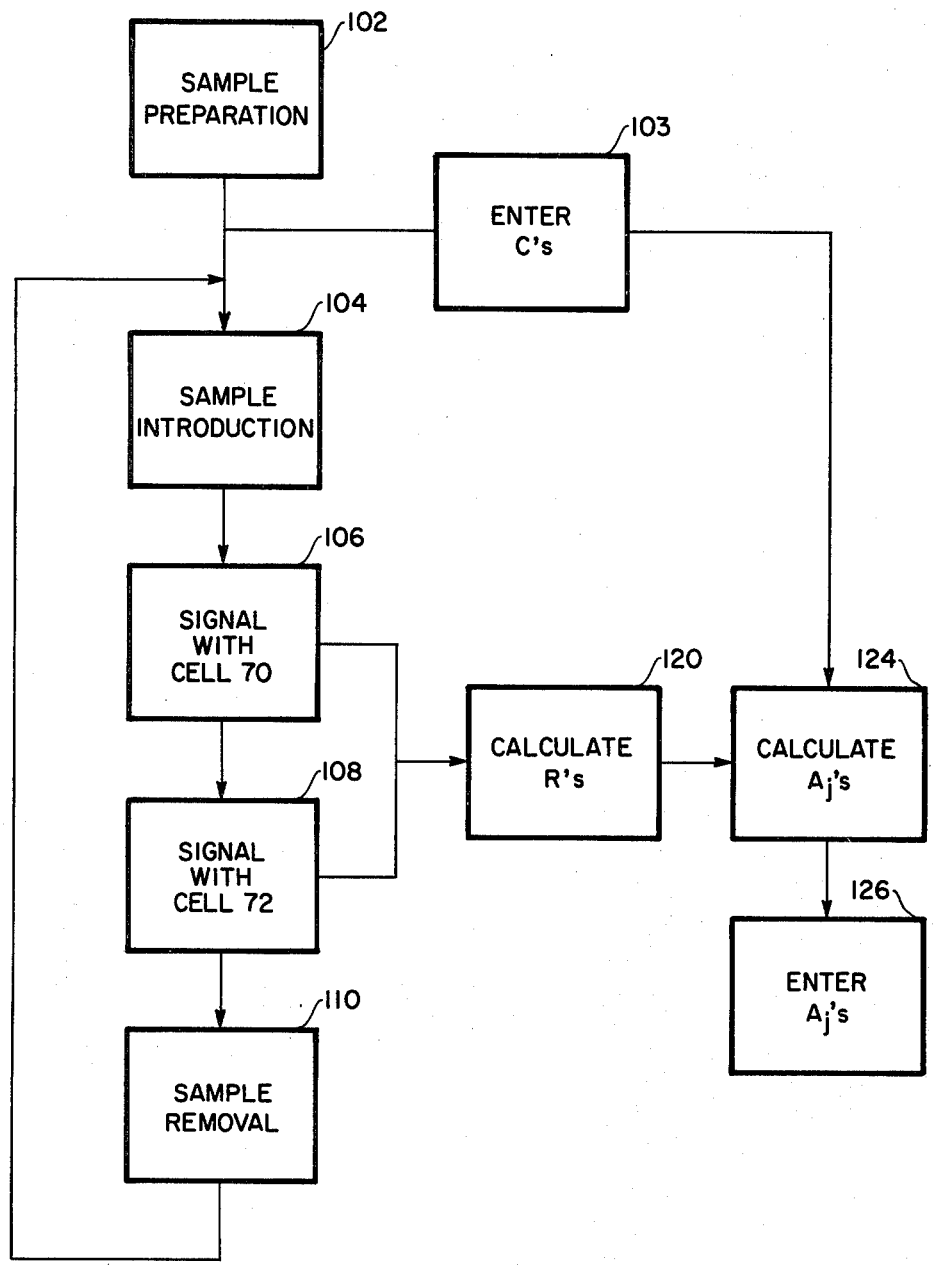
FIG. 2 is a block diagram illustrating the steps of the preferred embodiment of the present process.

It should be understood that before the analyzer described above can be used to achieve accurate results it must be calibrated. The calibration process according to the preferred embodiment of the present invention can be understood with reference to FIG. 2 which schematically illustrates the steps of the process.

Initially, a series of samples of calibration gas are prepared, each sample containing a different, known concentration of a preselected combustion gas. For example, if it is desired to calibrate the analyzer to measure carbon monoxide (CO), in practice I have found satisfactory samples to be of a mixture of nitrogen gas and CO, containing respectively 99, 195, 504, 774, 1204, 1796, 2087, and 2057 parts per million (ppm) CO. The sample preparation step is numbered 102 in FIG. 2.

After the sample preparation step 102 has been completed, the values of the concentration of combustion gas are entered into the computer 21 according to step 103. Then the analyzer is activated and the first member of the series of calibration gas samples is transferred from container 49 into the probe 19 according to the introduction step 104. After the probe 19 has been completely filled with the sample, the disc 68 is rotated, and when the $N_2$-filled cylinder 70 is interposed in the beam of radiation, the signal $S_iN_2$ is generated by the detector 18 and stored in the computer 21 according to step 106. Then the cell 72 containing CO is interposed in the beam of radiation, and a signal $S_iCO$ is generated by the detector 18 according to step 108 and stored in the computer 43.

After completion of the signal generation and storage step 108 the first calibration gas sample is removed from the probe 19 according to step 110, the second member of the series of calibration gases is introduced into the probe 19, and steps 104 through 110 are repeated for each member of the series of gases. Thus a series of n signals, $S_1$ through $S_n$ and a corresponding series of n signals $S_1CO$ through $S_nCO$ are stored in the computer. The stored signals are operated upon by the computer according to step 120 to calculate a series of ratios, $R_1$ through $R_n$ according to the formula:

$$R_i = S_iN_2/S_iCO \tag{1}$$

The values of ratios $R_i$ and the stored concentrations $C_i$ are operated upon by the computer according to step 124 to determine values for $A_j$ in the following equation:

$$R_i = \frac{1}{N} \sum_{j=1}^{N} \exp(-A_j C_i) \tag{2}$$

In practice I have found that the determination of four values for $A_j$ (N=4) is satisfactory. The values of $A_j$ for some analyzers range from about 10 to $10^{-6}$. After the values of $A_j$ have been calculated according to step 124, the values of $A_j$ are stored in the computer operating system 21 according to step 126. This step can be termed entry of data into the computer system of the analyzer.

It should be understood that the process described above for calibration for CO is substantially the same for $CO_2$. The analyzer can also be calibrated to measure other gases such as sulfur dioxide ($SO_2$) and nitrogen oxide (NO).

In operation of the analyzer, a gas having unknown concentrations of CO and $CO_2$ is introduced into the probe 19. The cells 70, 72 and 74 are sequentially introduced into the path of radiation and signals from the detector are stored for each cell. The ratios of the appropriate signals are calculated, and the computer utilizes the stored values of $A_j$ and the calculated ratios to calculate the concentration of CO and $CO_2$ by formula (2) above.

It can be appreciated that the present process is free of the types of error which were common in prior calibration methods. For example, in some prior calibration processes an operator plotted on graph paper the various values of the ratio, $R_i$ versus the actual concentration $C_i$ and attempted to draw a smooth curve through plotted points. Then, the curve was used to determine the concentration of an unknown gas, by an operator who identified the value of $R_i$ on one axis of the graph and read the concentration from the other axis. Operator error could be introduced in both steps of this process.

In contrast to the prior calibration process, the present process does not require a graph to be drawn; rather, coefficient $A_j$ are calculated. Furthermore, it is unnecessary to read a graph; rather, the coefficients $A_j$ are used to mathematically calculate the concentration.

The present process can be used to calibrate an analyzer for use in various processes. For example, the analyzer can be used as part of a control system such as the system taught in U.S. Pat. No. 4,359,950 issued Nov. 23, 1982 for "Method for Maximizing the Reduction Efficiency of a Recovery Boiler" which is incorporated by reference herein.

It should also be understood that although a particular gas analyzer is taught herein, this invention is not limited to any particular type of analyzer.

I claim:

1. A process for calibrating a computer-based combustion gas analyzer, said process comprising:
    (a) sequentially introducing into and removing from the analyzer, members of a series of calibration gases each having a different, known concentration ($C_i$) of the combustion gas;
    (b) generating a series of measurement values ($R_i$) to correspond, one to each known concentration ($C_i$) of combustion gas;
    (c) determining the coefficients $A_j$ in the equation:

$$R_i = \frac{1}{N} \sum_{j=1}^{N} \exp(-A_j C_i)$$

(d) entering the coefficients $A_j$ into the computer of the analyzer.

2. A process according to claim 1 wherein the combustion gas is carbon monoxide (CO).

3. A process according to claim 1 wherein the combustion gas is carbon dioxide ($CO_2$).

4. A process according to claim 1 wherein the measurement values ($R_i$) are produced according to the following steps:
    (a) transmitting a beam of radiation through the calibration gas to impinge upon a detector forming part of the analyzer;
    (b) generating a first signal according to the radiation transmitted through the gas and impinging on the detector;
    (c) transmitting a beam of radiation through the calibration gas and through a cell filled with substantially pure combustion gas to thereafter impinge upon the detector;
    (d) generating a second signal according to the radiation transmitted through the gas and the cell and impinging on the detector;
    (e) calculating a measurement value ($R_i$) according to the ratio of the first and second signals.

5. A process according to claim 1 wherein the values of the coefficient $A_j$ are between about 10 to $10^{-6}$.

6. A process for utilizing a combustion gas analyzer to control a fuel-burning system which generates combustion gases, said process comprising:
    (a) directing a beam of radiation through the combustion gases to impinge upon a detector forming part of the combustion gas analyzer;
    (b) in the analyzer, generating a value ($R_i$) corresponding to the concentration (C) of a constituent of the combustion gases;
    (c) calculating the concentration ($C_i$) of the constituent by the following equation:

$$R_i = \frac{1}{N} \sum_{j=1}^{N} \exp(-A_j C_i)$$

in which the values of $A_j$ are predetermined; and
    (d) utilizing the calculated concentration ($C_i$) to control the fuel-burning system.

7. A system for calibrating a combustion gas analyzer having a computer, said system comprising:
    (a) means to sequentially introduce into and remove from the analyzer a series of calibration gases each having a different, known concentration ($C_i$) of the combustion gas;
    (b) means to receive a series of measurement values ($R_i$) from the analyzer wherein each measurement value corresponds to the concentration ($C_i$) of each calibration gas, said means including means to determine the coefficients $A_j$ in the equation:

$$R_i = \frac{1}{N} \sum_{j=1}^{N} \exp(-A_j C_i)$$

(c) means for entering the coefficients $A_j$ into the computer operating system of the analyzer.

* * * * *